United States Patent [19]

Ueno et al.

[11] Patent Number: 4,894,359

[45] Date of Patent: Jan. 16, 1990

[54] HEAT-SENSITIVE RECORDING PAPER

[75] Inventors: Ryuzo Ueno, Nishinomiya; Shinichi Katsura, Toyonaka; Yoshirou Uchiyama, Nishinomiya; Satomi Inoue, Osaka, all of Japan

[73] Assignee: Kabushiki Kaisha Ueno Seiyaku Oyo Kenkyujo, Japan

[21] Appl. No.: 200,553

[22] Filed: May 31, 1988

Related U.S. Application Data

[62] Division of Ser. No. 66,476, Jun. 26, 1987, Pat. No. 4,855,482.

[30] Foreign Application Priority Data

Feb. 7, 1986 [JP] Japan ................................. 61-154233

[51] Int. Cl.$^4$ .............................................. B41M 5/18
[52] U.S. Cl. ..................................... 503/209; 428/913; 503/208; 503/216
[58] Field of Search ................................. 427/150–152; 428/913, 914; 503/208, 209, 216

[56] References Cited

U.S. PATENT DOCUMENTS

| 4,573,062 | 2/1986 | Satake et al. | 503/209 |
| 4,628,336 | 12/1986 | Satake et al. | 503/209 |

FOREIGN PATENT DOCUMENTS

| 1217065 | 5/1966 | Fed. Rep. of Germany | 428/480 |
| 2612842 | 10/1977 | Fed. Rep. of Germany | 428/480 |
| 2633096 | 1/1978 | Fed. Rep. of Germany | 428/480 |

*Primary Examiner*—Bruce H. Hess
*Attorney, Agent, or Firm*—Saidman, Sterne, Kessler & Goldstein

[57] ABSTRACT

The present invention provides a novel bis(phenoxymethyl)benzene derivative or bis(naphthoxymethyl)benzene derivative, which improves the stability of image on a heat sensitive recording paper composed of a leuco dye and a developer.

10 Claims, No Drawings

HEAT-SENSITIVE RECORDING PAPER

This application is a division, of application Ser. No. 066,476, filed June 26, 1987 U.S. Pat. No. 4,855,482.

BACKGROUND OF THE INVENTION

The present invention relates to bis(phenoxymethyl- and naphthoxymethyl)benzene derivatives which have been newly developed and their application to a heat sensitive recording paper.

In general, a heat sensitive recording paper in wide use is of the type in which a paper substrate is provided thereon with a colorant which is a colorless or pale-colored dye referred to as a leuco dye hereinafter, a phenolic compound which, as a developer, makes such a colorant assume a color when heated, a binder, a filler, an excipient, a lubricant, and other auxiliaries.

A heat sensitive recording paper produces an image in color by an instantaneous chemical reaction between a colorant and a developer when heat is applied thereto, and the applicability has been expanded from the use for copying of documents and printed matter into thermal pen type recorders in instrumentation, thermal printers, heat sensitive type automatic ticket vending machines, facsimile, etc. Especially where the application is in the information-related areas such as facsimile, demand is high for speedier operation of the apparatuses and therefore, heat sensitive recording paper used therein is required to have an ability to produce recording images of high densities speedily.

In the application of a phenolic compound as a developer, p-hydroxybenzoic acid esters, especially benzyl p-hydroxybenzoate, are known to be suitable for high speed heat sensitive recording (reference: Japanese Patent Publication Toku Kai Nos. Sho 52-140483, 56-144193, 57-82089 and 57-107885). A heat sensitive recording paper containing one of such developers lends itself to speeding up heat sensitive recording, showing a good coloring effect, producing brilliant recording images of high densities, and the plain surface being impaired much less by fog. However, the recording images developed are lacking in stability, fading and white spotting of the developed images being known as the defects. Although the reason for these defects may not always be clear, this instability is identified as crystallization of the p-hydroxybenzoic acid ester by loosening itself from the charge-transfer complex of the colorant and the p-hydroxybenzoate. It has been attempted to prevent this crystallization by addition of a certain compound but the result is not quite satisfactory.

With the above-mentioned defects taken into account the present inventors, in their research on heat sensitive recording paper, discovered new compounds which prevent the fading and the white spotting and brought the research to this invention.

SUMMARY OF THE INVENTION

The present invention provides a novel compound represented by a formula:

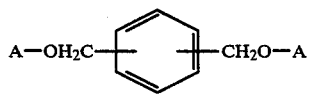

I wherein: A represents a group

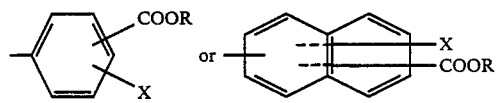

where R represents a $C_1$–$C_4$ alkyl group, phenyl group or benzyl group, and X represents hydrogen atom or halogen atom.

The compounds improve the stability of image on a heat sensitive recording paper composed of a leuco dye and a developer, especially phenolic hydroxyl group-containing acid esters.

DETAILED DESCRIPTION OF THE INVENTION

The first object of the present invention is to provide a bis(phenoxymethyl)benzene derivative or bis(naphthoxymethyl)benzene derivative, expressed by a general formula:

I wherein: A represents a group

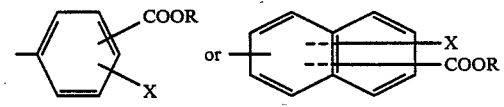

where R represents a $C_1$–$C_4$ alkyl group, phenyl group or benzyl group and X represents hydrogen atom or halogen atom.

The second object of the present invention is to provide a color forming composition for a heat sensitive recording paper, which contains the above compounds represented by the formula I, leuco dye and phenolic compound as an essential material on a sheet.

The third object of the present invention is to provide a heat sensitive recording paper which contains in its heat sensitive layer a leuco dye, developer, and one of the compounds expressed by a general formula I.

The compound expressed by the formula I can be produced, for example, by dehydrohalogenation between an alkaline salt of an aromatic hydroxycarboxylic acid ester which is expressed by a general formula:

 A—OH

II wherein: A is the same as in Formula I, and xylylene dihalogenoid which is expressed by a general formula

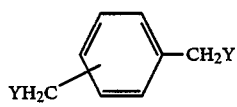

III wherein Y represents a halogen atom.

The alkaline salt of the compound expressed by the formula II may be, for example, a sodium salt or a potassium salt.

It is preferable to have this reaction take place in the presence of a solvent. The solvent suitable for this purpose is a polar aprotic solvent, such as N,N-dimethylformamide, N,N-dimethylacetamide or dimethyl sulfoxide. The reaction takes place for 1–8 hours at temperatures 50°–150° C.

After the reaction water is added to the reaction liquid and the precipitate is filtered out from the liquid and recrystallized into a refined compound expressed by said formula I.

The compounds expressed by said formula I include:

1,2-, 1,3- or 1,4-bis(o-carboalkoxy-phenoxymethyl)benzene,
1,2-, 1,3- or 1,4-bis(m-carboalkoxy-phenoxymethyl)benzene,
1,2-, 1,3- or 1,4-bis(p-carboalkoxy-phenoxymethyl)benzene,
1,2-, 1,3- or 1,4-bis(2-carboalkoxy-1-naphthoxymethyl)benzene,
1,2-, 1,3- or 1,4-bis(4-carboalkoxy-1-naphthoxymethyl)benzene,
1,2-, 1,3- or 1,4-bis(1-carboalkoxy-2-naphthoxymethyl)benzene,
1,2-, 1,3- or 1,4-bis(3-carboalkoxy-2-naphthoxymethyl)benzene, and
1,2-, 1,3- or 1,4-bis(6-carboalkoxy-2-naphthoxymethyl)benzene, and a compound such as one of the above which contains a carbophenoxy group or a carbobenzyloxy group instead of a carboalkoxy group.

Further, the compounds of the present invention include any compounds of which phenoxy or naphthoxy group has halogen substituents such as chloro-, bromo-, fluoro- and iodo-substituent. The position of the substituent is not restricted. Examples of the compound of which phenoxy or naphthoxy group is substituted with halogen are:

1,2-, 1,3- or 1,4-bis(2-halogeno-4-carbobenzyloxy-phenoxymethyl)benzene,
1,2-, 1,3- or 1,4-bis(3-halogeno-4-carbobenzyloxy-phenoxymethyl)benzene,
1,2-, 1,3- or 1,4-bis(3-halogeno-2-carbobenzyloxy-phenoxymethyl)benzene,
1,2-, 1,3- or 1,4-bis(4-halogeno-2-carbobenzyloxy-phenoxymethyl)benzene,
1,2-, 1,3- or 1,4-bis(2-halogeno-4-carboalkoxyphenoxymethyl)benzene,
1,2-, 1,3- or 1,4-bis(3-halogeno-4-carboalkoxyphenoxymethyl)benzene,
1,2-, 1,3- or 1,4-bis(4-halogeno-2-carboalkoxyphenoxymethyl)benzene,
1,2-, 1,3- or 1,4-bis(2-halogeno-3-carboalkoxyphenoxymethyl)benzene,
1,2-, 1,3- or 1,4-bis(2-halogeno-4-carboalkoxy-1-naphthoxymethyl)benzene,
1,2-, 1,3- or 1,4-bis(4-halogeno-2-carboalkoxy-1-naphthoxymethyl)benzene,
1,2-, 1,3- or 1,4-bis(6-halogeno-2-carboalkoxy-1-naphthoxymethyl)benzene,
1,2-, 1,3- or 1,4-bis(8-halogeno-4-carboalkoxy-1-naphthoxymethyl)benzene,
1,2-, 1,3- or 1,4-bis(8-halogeno-6-carboalkoxy-1-naphthoxymethyl)benzene,
1,2-, 1,3- or 1,4-bis(1-halogeno-4-carboalkoxy-2-naphthoxymethyl)benzene,
1,2-, 1,3- or 1,4-bis(4-halogeno-1-carboalkoxy-2-naphthoxymethyl)benzene,
1,2-, 1,3- or 1,4-bis(6-halogeno-8-carboalkoxy-2-naphthoxymethyl)benzene,
1,2-, 1,3- or 1,4-bis(8-halogeno-6-carboalkoxy-2-naphthoxymethyl)benzene,
1,2-, 1,3- or 1,4-bis(4-halogeno-6-carboalkoxy-2-naphthoxymethyl)benzene,
1,2-, 1,3- or 1,4-bis(1-halogeno-8-carboalkoxy-2-naphthoxymethyl)benzene, and the like.

The carboalkoxy group in a compound expressed by the formula I may be, for example, carbomethoxy group, carboethoxy group, carbopropoxy group, or carbobutoxy group.

In producing a heat sensitive recording paper according to the present invention, a leuco dye, a developer, and a compound expressed by the formula I are compounded: for 100 parts by weight of a leuco dye 100–1000 parts by weight of a developer is preferably employed, and for 100 parts by weight of a developer a compound expressed by the formula I is preferably employed in a proportion in the range 1–200, especially 3–100 parts by weight.

The leuco dyes applicable to the practice of this invention, for example, include those of the types of triphenylmethane, fluoran, phenothiazine, auramine, and spiropyran. These dyes are employed each singly or in a mixture of two dyes or more. Some examples of these leuco dyes are as follows:

3,3-bis(p-dimethylaminophenyl)phthalide,
3,3-bis(p-dimethylaminophenyl)-6-dimethylaminophthalide,
(called also crystal violet lactone),
3,3-bis(p-dimethylaminophenyl)-6-diethylaminophthalide,
3,3-bis(p-dimethylaminophenyl)-6-chlorphthalide,
3,3-bis(p-dibutylaminophenyl)phthalide,
3-cyclohexylamino-6-chlorfluoran,
3-dimethylamino-5,7-dimethylfluoran,
3-diethylamino-7-chlorofluoran,
3-diethylamino-7-methylfluoran,
3-diethylamino-7,8-benzfluoran,
3-diethylamino-6-methyl-7-chlorfluoran,
3-(N-p-tolyl-N-ethylamino)-6-methyl-7-anilinofluoran,
3-pyrrolidino-6-methyl-7-anilinofluoran,
2-N-(3'-trifluormethylphenyl)amino-6-diethylaminofluoran,
2-3,6-bis(diethylamino)-9-(o-chloranilino)xanthylium benzoic acid lactam,
3-diethylamino-6-methyl-7-(m-trichloromethylanilino)-fluoran,
3-diethylamino-7-(o-chloranilino)fluoran,
3-dibutylamino-7-(o-chloranilino)fluoran,
3-N-methyl-N-amylamino-6-methyl-7-anilinofluoran,
3-N-methyl-N-cyclohexylamino-6-methyl-7-anilinofluoran,
3-diethylamino-6-methyl-7-anilinofluoran,
3-(N,N-diethylamino)-5-methyl-7-(N,N-dibenzylamino)fluoran, benzoyl leucomethylene blue,
6'-chloro-8'-methoxy-benzoindolyno-pyrylospiran,
6'-bromo-3'-methoxy-benzoindolyno-pyrylospiran,
3-(2'-hydroxy-4'-dimethylaminophenyl)-3-(2'-methoxy-5'-chlor-phenyl)phthalide,
3-(2'-hydroxy-4'-dimethylaminophenyl)-3-(2'-methoxy-5'-nitro-phenyl)phthalide,
3-(2'-hydroxy-4'-diethylaminophenyl)-3-(2'-methoxy-5'-methyl-phenyl)phthalide,
3-(2'-methoxy-4'-dimethylaminophenyl)-3-(2'-hydroxy-4'-chlor-5'-methylphenyl)phthalide,
3-morpholino-7-(N-propyl-trifluoromethylanilino)fluoran,
3-pyrrolidino-7-trifluoromethylanilinofluoran, 3-diethylamino-5-chloro-7-(N-benzyl-trifluoromethylanilino)fluoran,
3-pyrrolidino-7-(di-p-chlorphenyl)methylaminofluoran,
3-diethylamino-5-chlor-7-(α-phenylethylamino)fluoran,
3-(N-ethyl-p-toluidino)-7-(α-phenylethylamino)fluoran,
3-diethylamino-7-(o-methoxycarbonylphenylamino)-fluoran,
3-diethylamino-5-methyl-7-(α-phenylethylamino)fluoran,
3-diethylamino-7-piperidinofluoran,
2-chloro-3-(N-methyltoluidino)-7-(p-n-butylanilino)-fluoran,
3-(N-benzyl-N-cyclohexylamino)-5,6-benzo-7-α-naphthylamino-4'-bromofluoran, and
3-diethylamino-6-methyl-7-mesitydino-4',5'-benzofluoran.

The developers used in the heat sensitive printing paper may be phenolic hydroxyl group containing compounds which have been used in a conventional heat sensitive printing paper. Preferable phenolic compounds are esters of mono- or polyphenols having a hydroxyl group and carboxyl group such as hydroxybenzoic acid esters, alkyl gallate, tannic acid esters and the like. The most preferable one is p-hydroxybenzoate such as methyl p-hydroxybenzoate, ethyl-, propyl-, isopropyl-, butyl-, isobutyl-, hexyl-, benzyl-, phenetyl-, phenyl-, or naphthyl p-hydroxybenzoate.

In order to prepare the color forming composition for the heat sensitive printing paper according to the present invention the compound represented by the formula I, the developer and leuco dye may be mixed under the condition that the melted compound and developer are not contacted with the leuco dye. The color forming composition may be a dispersion type, solution type and hot-melt type, but the solution type and the hot melt type must be separated in order to prevent color developing before use. Most preferable color forming composition composition is a dispersion type, especially dispersion-in-water type.

In order to prepare the dispersion type composition the compound represented by the formula I alone or with the developer is dispersed in a suitable medium such as water, and mixed with dye which is also dispersed in a medium such as water. The compound represented by the formula I and developer may be separately dispersed or the both may be homogenously mixed, fused and powdered before the dispersion.

At the dispersion these materials are ground into fine particles in a medium, especially water by means of a grinder, such as a ball mill, Atrighter or sand-grinder, or by means of a suitable emulsifying means and prepared, together with additives, into liquid coatings.

The additives used to make the color forming composition are, for example, a binder, for which are used polyvinyl alcohol, hydroxyethyl cellulose, methyl cellulose, starch, styrene-maleic anhydride copolymer, vinylacetate-maleic anhydride copolymer, styrene-butadiene copolymer, etc., a filler, for which are used kaolin, diatomaceous earth, talc, titanium oxide, calcium carbonate, magnesium carbonate, aluminum hydroxide, etc., an excipient, for which are used fatty acid metallic salts such as zinc stearate, aluminum stearate, calcium stearate, zinc oleate, etc., a lubricating agent, for which are used waxes such as paraffin wax, carnauba wax, polyethylene wax, etc., a UV ray absorbent, for which benzophenones and triazoles are used, a waterproofing agent such as glyoxal, a dispersion liquid, a defoaming agent, etc.

A heat sensitive recording paper provided by the present invention is obtained by coating a substrate, such as paper or film, with a color forming composition prepared as above with use of additives. If desired, a heat sensitive recording paper having two layer, e.g. leuco dye layer and developer layer with the compound represented the formula I on paper may be prepared.

A heat sensitive recording paper thus obtained according to the present invention exhibits advantages in good coloring effect, adaptability to high speed recording, and stability of the coating, and the images produced thereon show an excellent stability with improvement in the liability to fading and white spotting.

EXAMPLE 1

Synthesis of 1,3-bis(p-carbobenzyloxyphenoxymethyl)-benzene

To a solution of p-hydroxybenzoic acid benzyl ester (45.6 g, 0.2 mol) in 200 ml N,N-dimethylformamide, sodium carbonate (10.6 g, 0.1 mol) was added and stirred for 10 minutes at room temperature. Then a solution of m-xylylenedichloride (17.3 g, 0.1 mol) in 100 ml of N,N-dimethylformamide was added in drops to the reaction mixture in 10 minutes. The reaction mixture stirred at 113° C. for 4 hours, cooled and blown into water, and the obtained precipitate was filtered, rinsed with water. Then crued product was suspended in methanol and stirred at 60° C. for 30 minutes, cooled, filtered, and gave 15.8 g (yield 26.9%) of 1,3-bis(p-carbobenzyloxyphenoxymethyl)-benzene: m.p. 92.5°–93.8° C.

NMR value: δ 5.11 (4H, s), 5.33 (4H, s), 6.91–8.07 (22H, m).

Mass value: m/z=558 (M+).

| Element analysis values | | | |
| --- | --- | --- | --- |
| | C | H | O |
| Calculated value (%) | 77.4 | 5.4 | 17.2 |
| Measured value (%) | 76.8 | 5.5 | 17.7 |

EXAMPLE 2

Synthesis of 1,4-bis(p-carbobenzyloxyphenoxymethyl)benzene

To a solution of p-hydroxybenzoic acid benzyl ester (68.4 g, 0.3 mol) in N,N-dimethylformamide (274 g) sodium carbonate (15.9 g, 0.15 mol) was added, and stirred at 100° C. Then, p-xylylenedichloride (26.2 g, 0.15 mol) was added to the reaction mixture in 10 minutes, and stirred at 100° C. for one hour. Water was added to the resultant to separate a clued precipitate. The precipitate was filtered, added to N,N-dimethylformamide to be dissolved at 90° C., cooled, filtered, and dried to give a white crystal of 1,4-bis(p-carbobenzyloxyphenoxymethyl)benzene (27.8 g, yield 33.0): m.p. 154°–157° C.

NMR values: δ 5.11 (4H, s), 5.33 (4H, s), 6.92–8.07 (22H, m).

Mass value: m/z=558 (M+).

| Element analysis values | | | |
| --- | --- | --- | --- |
| | C | H | O |
| Calculated value (%) | 77.4 | 5.4 | 17.2 |
| Measured value (%) | 76.8 | 5.5 | 17.7 |

EXAMPLE 3

Synthesis of 1,3-bis(6-carbomethoxy-2-naphthoxymethyl)benzene

To sodium salt of 2-hydroxynaphthalene-6-carboxylic acid methyl ester (44.8 g) N,N-dimethylformamide (200 ml) was added with stirring at room temperature. Then a solution of m-xylylenedichloride (17.5 g, 0.1 mol) in N,N-dimethylformamide was added in drops thereto in 10 minutes. The reaction mixture was stirred at 105° C. for 4 hours and then cooled to give a precipitate. The precipitate was rinsed with N,N-dimethylformamide, treated with hot water at 80° C. for 30 minutes with stirring, and then with methanol at 60° C. for 30 minutes with stirring; cooled, filtered and dried to give a white crystals of 1,3-bis(6-carbomethoxy-2-naphthoxymethyl)benzene (39.7 g, yield 77.8%): m.p. 177.3°–178.0° C.

NMR values: δ 3.95 (6H, s), 5.21 (4H, s), 7.20–8.52 (16H, m).

Mass value: m/z=506 (M+)

| Element analysis values | | | |
|---|---|---|---|
| | C | H | O |
| Calculated value (%) | 75.8 | 5.1 | 19.1 |
| Measured value (%) | 75.7 | 5.2 | 19.1 |

EXAMPLE 4

Synthesis of 1,3-bis(m-carbomethoxyphenoxymethyl)benzene

To a solution of m-hydroxybenzoic acid methyl ester (30.4 g, 0.2 mol) in 150 ml methanol sodium methylate (38.6 g, 0.2 mol) was added. The mixture was stirred at 100° C. for one hour, cooled and dried. To the dried product N,N-dimethylformamide (150 ml) was added and then m-xylylenedichloride (17.5 g, 0.1 mol); and stirred at 110° C. for 2 hours. After cooled, the precipitate was filtered off, and the obtained filtrate was blown into water-methanol (1:1) and then filtered. The precipitate obtained was treated with methanol, and dried to give a white crystale of 1,3-bis(m-carbomethoxyphenoxymethyl)benzene (28.3 g, yield 69.7%): m.p. 57.8–58.5.

EXAMPLE 5

Synthesis of 1,4-bis(o-carbomethoxyphenoxymethyl)benzene

To a solution of salicylic acid methyl ester (45.6 g, 0.3 mol) in 150 ml N,N-dimethylformamide sodium carbonate (18.0 g, 0.17 mol) was added, stirred at 100° C., and then p-xylylenedichloride (29.8 g, 0.17 mol) was added thereto. The mixture was reacted at 144° C. for 8 hours. After the reaction, the obtained mixture was cooled and blown into water to give a precipitate, which was then filtered. The filtered precipitate was treated with hot methanol and dried to give a white crystal of 1,4-bis(o-carbomethoxyphenoxymethyl)benzene (8.3 g, yield 14%): m.p. 115°–120° C.

EXAMPLE 6

Synthesis of 1,3-bis(2-chloro-4-carbobenzyloxyphenoxymethyl)-benzene

To a solution of 2-chloro-4-hydroxybenzoic acid benzyl ester (26.3 g, 0.1 mol) in 100 ml N,N-dimethyl-formamide sodium carbonate (5.3 g, 0.05 mol) was added, and stirred for 10 minutes at room temperature. Then a solution m-xylylenedichloride (8.8 g, 0.05 mol) in 50 ml N,N-dimethylformamide was added in drops to the reaction mixture in 10 minutes. The reaction mixture is stirred at 120° C. for 2 hours, cooled and blown into water to give a precipitate. The obtained precipitate was filtered, and rinsed with water. Then crued product was suspended in methanol and stirred at 60° C. for 30 minutes, cooled and filtered, and gave a white drystal of 1,3-bis(2-chloro-4-carbobenzyloxy-phenoxymethyl)-benzene (25.2 g, yield 80%): m.p. 95.8°–97.0° C.

EXAMPLE 7

| Liquid A (dye-dispersed liquid) | |
|---|---|
| 3-(N—cyclohexyl-N—methylamino)-6-methyl-7-anilinofluoran | 4.0 parts |
| 10% polyvinyl alcohol water solution | 9.2 parts |
| water | 5.0 parts |
| Liquid B (developer-dispersed liquid) | |
| p-hydroxybenzoic acid benzyl ester | 6.0 parts |
| 1,3-bis(p-carbobenzyloxy-phenoxymethyl)benzene | 0.6 parts |
| 10% polyvinyl alcohol water solution | 30.0 parts |

The Liquids A and B were ground in a ball mill respectively, and 1.0 parts by weight of the Liquid A and 4.0 parts by weight of the Liquid B were mixed to prepare a color forming composition. The color forming composition was applied to a base paper by means of a wire bar to give a heat sensitive recording paper (coating 6 g/m²).

EXAMPLE 8

A heat sensitive recording paper was obtained in the same manner as in the example 7, except that 1,4-bis(p-carbobenzyloxy-phenoxymethyl)benzene was used instead of 1,3-bis(p-carbobenzyloxy-phenoxymethyl)benzene.

EXAMPLE 9

A heat sensitive recording paper was obtained in the same manner as in the example 7, except that 1,3-bis(6-carbomethoxy-2-naphthoxymethyl)benzene was used instead of 1,3-bis(p-carbobenzyloxy-phenoxymethyl)-benzene.

EXAMPLE 10

A heat sensitive reporting paper was obtained in the same manner as in the Example 7, except that 1,3-bis(2-chloro-4-carbobezyloxy-phenoxymethyl)benzene was used instead of 1,3-bis(p-carbobenzyloxy-phenoxymethyl) benzene.

REFERENCE EXAMPLE

A heat sensitive recording paper was obtained in the same manner as in the Example 7, except that 1,3-bis(p-carbobenzyloxy-phenxoymethyl)benzene was not used.

[EXPERIMENT 1]

Five kinds of heat sensitive recording paper, obtained in the examples 7–10 and in the Reference Example, were tested with respect to the plain surface and image density, first with the image developed at 120° C. and secondly when the heat sensitive recording paper was held for 24 hours under the conditions of (1) 40° C. and 90% humidity, and (2) 60° C. The results are shown in Table 1. A heat sensitive recording paper of the present invention apparently showed a less variation in image density with time, and was excellent in a keeping stability in comparison with the heat sensitive recording paper in the Reference Example.

TABLE 1

|  | Image density when developed | Image preservation stability | | | | Plain surface | | |
|---|---|---|---|---|---|---|---|---|
|  |  | After 24 hours standing at 40° C. and 90% humidity | | After 24 hours' standing at 60° C. | | Density before test | After 24 hours' standing at 40° C. and 90% humidity | After 24 hours' standing at 60° C. |
|  |  | Preservation rate (%) | Appearance | Preservation rate (%) | Apperance |  |  |  |
| Example 7 | 1.07 | 100 | O | 118 | O | 0.13 | 0.13 | 0.14 |
| Example 8 | 0.94 | 93 | O | 98 | O | 0.12 | 0.14 | 0.14 |
| Example 9 | 1.01 | 88 | O | 126 | O | 0.12 | 0.13 | 0.14 |
| Example 10 | 1.04 | 106 | O | 107 | O | 0.11 | 0.13 | 0.13 |
| Comparison | 1.26 | 83 | Δ | 84 | Δ | 0.13 | 0.13 | 0.15 |

O No or virtually no change
X Fades in mottles
Δ A few fades in mottles

[EXPERIMENT 2]

Two kinds of heat sensitive recording paper, obtained in the Example 7 and the Reference Example, were tested with respect to change of image density. They were subjected to a rigid condition of 60° C. and 90% humidity, under which they were held for 24 hours after development at 120° C. The results are shown in Table 2.

TABLE 2

|  | Image preservation stability | |
|---|---|---|
|  | Preservation rate (%) | Appearance |
| Example 7 | 101 | O |
| Reference Example | 74 | X |

O: No or virtually no change
X: Fades in mottles or white crystals separate out.

What is claimed is:

1. A heat sensitive recording paper which contains in its heat sensitive layer a leuco dye, developer, and either of a bis(phenoxymethyl)benzene derivative or bis(naphthoxymethyl)benzene derivative having the general formula (I):

wherein: A represents a group

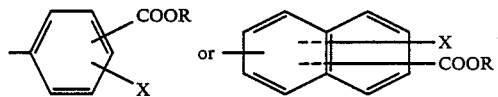

where R represents a $C_1$-$C_4$ alkyl group, a phenyl group or benzyl group, and X represents hydrogen atom or halogen atom.

2. The heat sensitive recording paper of claim 1, wherein said developer is a phenolic hydroxyl group containing compound.

3. The heat sensitive recording paper of claim 1, wherein said developer is a hydroxybenzoic acid ester.

4. The heat sensitive recording paper of claim 1, wherein said leuco dye, developer and bis (phenoxymethyl) benzene derivative or bis (naphthoxymethyl) benzene derivative expressed by the formula (I) is dispersed in a liquid medium.

5. The heat sensitive recording paper of claim 4, wherein said liquid medium is water.

6. The heat sensitive recording paper of claim 1, wherein said developer is contained in a range of 100-1000 parts by weight based on 100 parts by weight of said leuco dye, and said compound represented by the formula (I) is in 1-200 parts by weight based on 100 parts by weight of said developer.

7. The heat-sensitive recording paper of claim 1, wherein said bis(naphthoxymethyl)benzene derivative is a 1,3 benzene derivative, wherein A is naphthylene, R is benzyl and X is hydrogen.

8. The heat-sensitive recording paper of claim 1, wherein said benzene derivative is a 1,2 benzene derivative, wherein A is naphthylene, R is benzyl an X is hydrogen.

9. The heat-sensitive recording paper of claim 1, wherein said benzene derivative is a 1,2 benzene derivative wherein A is naphthylene, R is $C_1$ alkyl and X is hydrogen.

10. The heat-sensitive recording paper of claim 1, wherein said benzene derivative is a 1,4 benzene derivative, wherein A is naphthylene, R is benzyl and X is hydrogen.

* * * * *